United States Patent [19]
Strasser et al.

[11] Patent Number: 5,867,561
[45] Date of Patent: Feb. 2, 1999

[54] MEDICAL DIAGNOSTIC IMAGING SYSTEM WITH POWER CONSERVING CONTROL APPARATUS

[75] Inventors: Scott A. Strasser, Mukwonago; John E. Dwyer, Jr., Muskego; Neil D. Mooers, Delafield; John E. Bechthold, Waukesha, all of Wis.

[73] Assignee: General Electric Company, Milwaukee, Wis.

[21] Appl. No.: 902,706

[22] Filed: Jul. 30, 1997

[51] Int. Cl.[6] ....................................................... A61B 5/00
[52] U.S. Cl. ......................... 378/98.2; 378/101; 378/114
[58] Field of Search ............................. 378/91, 101, 102, 378/103, 114, 117, 118, 193, 197, 198; 250/363.02; 600/407, 410, 413, 425, 428

[56] References Cited

U.S. PATENT DOCUMENTS

| | | | |
|---|---|---|---|
| 4,322,623 | 3/1982 | Grady ................................... | 378/198 X |
| 4,979,198 | 12/1990 | Malcolm et al. .................... | 378/198 X |
| 5,206,894 | 4/1993 | Makrinos et al. ................... | 378/114 X |
| 5,477,858 | 12/1995 | Norris et al. ............................. | 600/441 |
| 5,693,948 | 12/1997 | Sayed et al. ........................ | 378/98.8 X |

*Primary Examiner*—David P. Porta
*Attorney, Agent, or Firm*—James O. Skarsten; Christian G. Cabou; Phyllis Y. Price

[57] ABSTRACT

Control apparatus is provided for a medical diagnostic imaging system, such as a mobile X-ray unit. The imaging system includes a battery or like power storage device of limited capacity, and a number of components disposed to perform respective corresponding functions. The control apparatus includes a user interface for enabling an operator to generate commands which selectively direct the components to perform their respective corresponding functions. The control apparatus further includes a system control means, comprising a controller and set of control circuits, for initially placing the imaging system in a powered-up mode, wherein each component is coupled to receive power from the battery. A sleep mode activation device is included in the system control for decoupling a first set of components from the battery, while allowing a second set of components to remain coupled thereto, following a first time period during which no command is generated by the user interface. Each component of the second set performs a function which is required to enable the system control to recognize that a command has been generated.

11 Claims, 4 Drawing Sheets

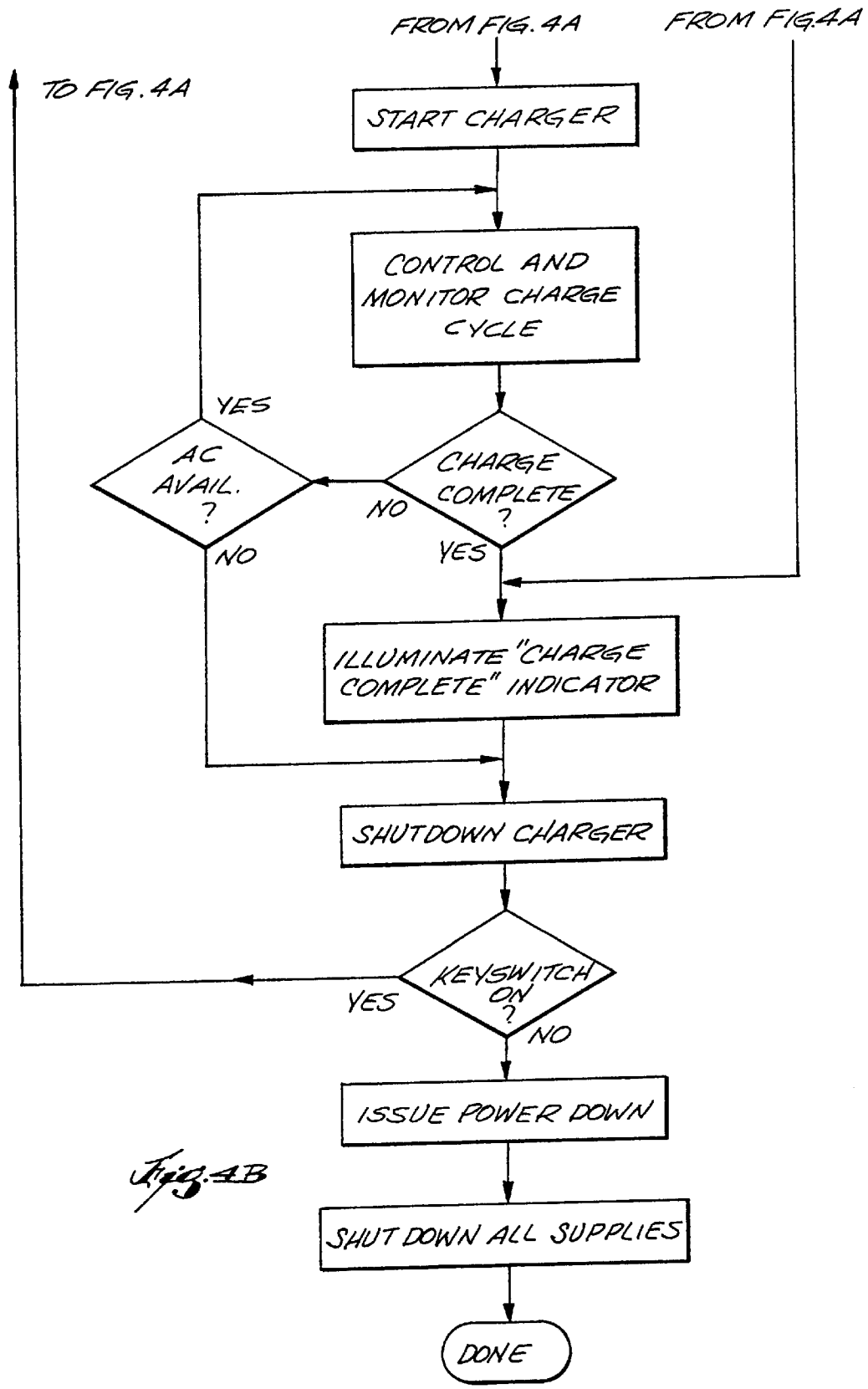

MEDICAL DIAGNOSTIC IMAGING SYSTEM WITH POWER CONSERVING CONTROL APPARATUS

BACKGROUND OF THE INVENTION

The invention disclosed and claimed herein is generally directed to apparatus for conserving power in a medical diagnostic imaging system, such as a mobile X-ray unit. More particularly, the invention is directed to apparatus of such type for use with a medical diagnostic imaging system operated by power from an electric battery or other device having a limited power storage capacity.

As is well known, the term "medical diagnostic imaging system" is generally applied to equipment which uses a radiographic or magnetic technique to provide images of internal human body structures. Such equipment includes X-ray, computed tomography (CT) and magnetic resonance (MR) imaging systems, although it is not limited thereto. As is further well known, these types of systems are comparatively expensive. Accordingly, system suppliers are increasingly interested in developing diagnostic imaging equipment which is portable or mobile, so that it can be readily moved from one location of use to another. The utility of such equipment may thereby be significantly enhanced. Developments of this type are exemplified by a product of the General Electric Company, which is known as the AMX-4 X-ray unit. This product comprises an X-ray machine mounted on a wheeled carriage and provided with a drive motor and steering controls. The motor is powered by a rechargeable battery likewise mounted on the X-ray unit. The unit can thus be easily moved, for example, from one room to another in a hospital.

In mobile units of the above type, it has been found useful to employ the storage battery to operate respective X-ray imaging components, such as the generator, inverter and rotor controller, in addition to operating the unit drive motor. This arrangement minimizes components. Moreover, such arrangement enables the unit to be readily moved from one X-ray site to another, and then operated at the new site without concern about the availability of an external power source, such as an electric outlet of suitable voltage. However, the power storage capacity of a single battery is limited, and such dual use may tend to draw battery power down quickly under certain conditions. While the battery can be recharged when the X-ray unit is not in use, the needs of a health care environment are sometimes very unpredictable. For example, a series of medical emergencies could arise, requiring continuous use of the X-ray unit over an extended period of time, without opportunity to recharge the battery. If battery power was low at the beginning of the period, or if the unit consumed power unnecessarily, the battery might become depleted when power was still needed to acquire X-ray exposures of a patient. Thus, in such mobile X-ray and other diagnostic imaging equipment, it would be desirable to conserve or minimize use of battery power as much as possible. In some circumstances, it could be significantly beneficial to conserve even comparatively small amounts of power, if such conservation would enable the battery to acquire several additional X-ray exposures. It could also be desirable to minimize strain on the battery during recharging procedures.

SUMMARY OF THE INVENTION

The invention generally comprises control apparatus for a medical diagnostic imaging system, wherein the imaging system includes a power storage device of limited capacity, such as a battery, and a number of sub-systems. The sub-systems are respectively activated, when they receive power from the storage device, to perform respective specified tasks. A given one of the sub-systems includes a number of specified components disposed to receive power from the storage device when the imaging system is in a powered-up mode, even if the given sub-system is not activated to perform its specified tasks. The apparatus of the invention comprises user interface means for enabling a user or operator to generate input commands, at least some of the commands directing activation of sub-systems to perform their respective specified tasks. The apparatus further comprises a system control means receiving the commands, for coupling power from the storage device to activate sub-systems respectively corresponding to received commands. Sleep mode means are included in the system control means for disconnecting the specified components from the storage device at the end of a first time period, if the imaging system is in the powered-up mode and no command is received by the system control means during the first time period. Preferably, the sleep mode means further comprises means for reconnecting the specified components to the storage device, if a command is received after the end of the first time period, but prior to the end of a subsequent second time period. Preferably also, the system control means includes power shut-down means for taking the system out of its powered-up mode after disconnection of the specified components from the storage device, if no command is received prior to the end of the second time period.

In a preferred embodiment, the diagnostic imaging system comprises a mobile X-ray unit, which is mounted on a wheeled carriage or the like. One of the sub-systems comprises an electric drive motor, mechanically coupled to the wheels, and other components pertaining thereto. Such drive motor sub-system is activated to move the unit from one location to another. Another sub-system comprises an X-ray tube generator and related components, which are collectively operated to drive the tube to produce X-rays, and to acquire X-ray images. The power storage device comprises an electric battery of specified capacity, and the system control means comprises a controller, for generating control signals respectively representing input commands, and a set of control circuits operable in response to the control signals to selectively couple power from the battery to respective sub-systems.

It is anticipated that in the past, up to 25% of power usage was wasted in mobile units of the above type, i.e., was consumed by components drawing power when the unit was in a powered-up mode but was idle, that is, was not doing useful work. It is further anticipated that the present invention can substantially eliminate such waste.

OBJECTS OF THE INVENTION

An object of the invention is to provide apparatus for conserving or minimizing the use of power in connection with an X-ray or other diagnostic imaging unit.

Another object is to provide apparatus of the above type for use in connection with a mobile diagnostic imaging unit, wherein the power required both to move the unit and to operate its image forming sub-system must be supplied by a single storage battery or string of batteries mounted on the unit.

Another object is to provide apparatus of the above type which minimizes power consumption while the unit is in a powered-up mode but idle, e.g., during patient set up or when a user has forgotten to turn off the unit power source.

Another object is to provide apparatus of the above type wherein the battery is rechargeable, and includes a charging system which is designed to reduce stress on the battery and an associated charging circuit in the course of a battery charging operation.

These and other objects of the invention will become more readily apparent from the ensuing specification, taken together with the accompanying drawings.

BRIEF DESCRIPTION OF THE DRAWINGS

FIGS. 4a and 4b are flow chart illustrating a battery charging technique.

DETAILED DESCRIPTION OF THE PREFERRED EMBODIMENT

Figure 1:
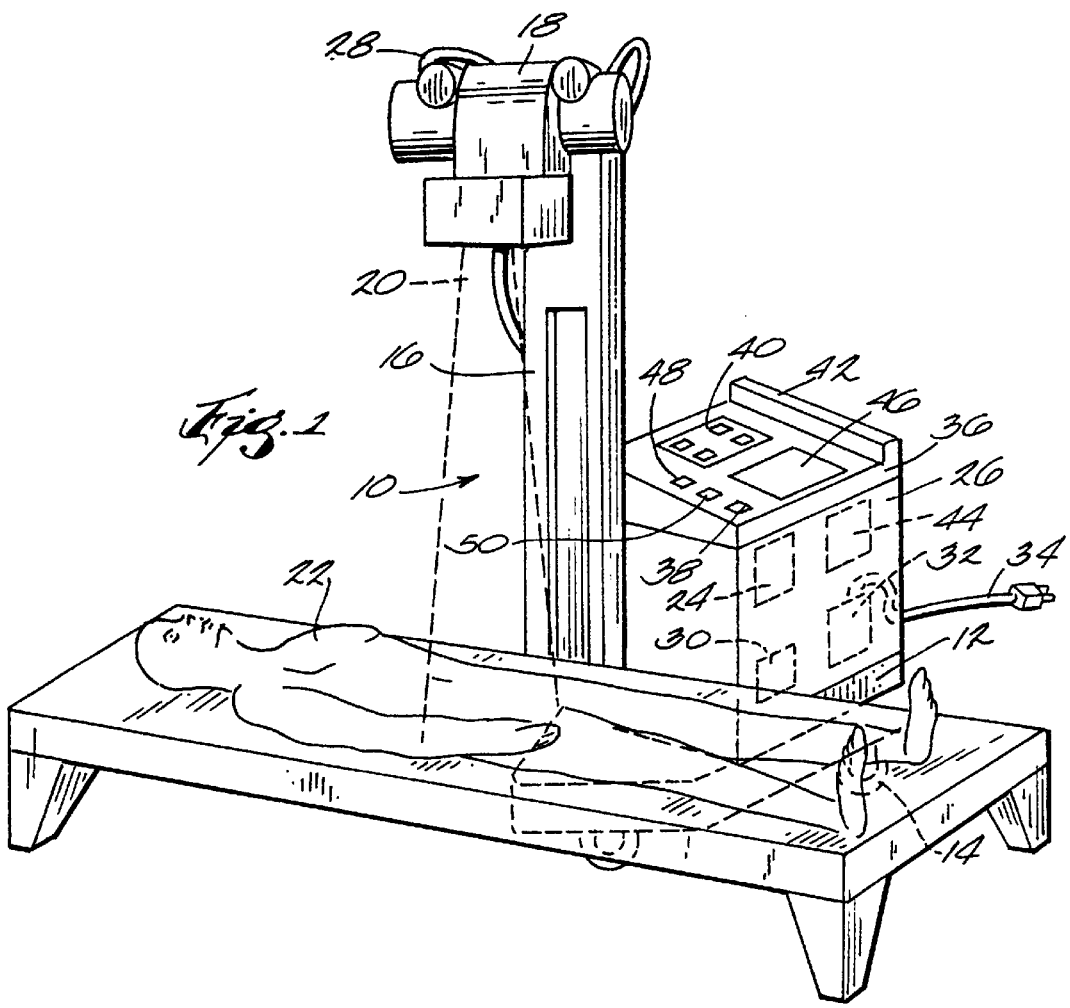
FIG. 1 is a perspective view showing an X-ray imaging unit provided with an embodiment of the invention.

Referring to FIG. 1, there is shown a mobile X-ray unit 10 usefully employing an embodiment of the invention. Unit 10 may comprise, for example, the aforementioned AMX-4 X-ray unit, but is not limited thereto. Unit 10 generally includes a carriage or platform 12 provided with wheels 14, whereby unit 10 may be readily moved or transported over a floor or other supportive horizontal surface (not shown). A column 16 extending upward from platform 12 supports a conventional X-ray tube 18, which produces a beam of X-radiation 20 for acquiring X-ray exposures of a patient 22. Usefully, column 16 is mounted for rotation relative to platform 12 about a vertical axis. In like manner, tube 18 is mounted for rotation relative to column 16 about a horizontal axis. Thus, X-ray tube 18 may be readily positioned to project X-ray beam 20 at a desired orientation with respect to the patient 22.

Referring further to FIG. 1, there is shown an X-ray imaging subsystem 24 contained in a housing 26 mounted on platform 12. Subsystem 24 includes a conventional generator (not shown) necessary to provide the very high electrical voltage required by tube 18 to produce X-rays. Subsystem 24 further comprises other conventional components and elements necessary to operate X-ray tube 18, including an inverter, a rotor controller, and filament drive logic (not shown). Such components and elements, some of which are referred to hereinafter, are considered to be very well known in the art. Electrical power required for operating tube 18 is coupled thereto from subsystem 24 through cables 28.

FIG. 1 further shows unit 10 provided with a second subsystem 30, likewise contained in housing 26, which comprises a conventional motor drive (not shown) and related components for supplying mechanical power to controllably move unit 10. Motive power may be coupled from motor drive subsystem 30 to the wheels 14 by means of a drive belt or other conventional means for transmitting mechanical power (not shown). Some of the components and elements included in drive subsystem 30 are referred to hereinafter.

Referring further to FIG. 1, there is shown an electrical storage battery 32 in housing 26 for supplying all of the power required for operation of mobile unit 10, including the needs of subsystems 24 and 30. Power is also needed from battery 32 to operate other electrical and electronic components, such as LED indicator lights, an operator display screen and system logic. Battery 32 usefully comprises a string of sealed lead acid batteries, which is rechargeable by connecting a power cord 34 to a 110 volt or 220 volt AC source, as required.

To control operation of X-ray unit 10, a user interface console 36 is mounted on the top of housing 26. Console 36 includes a key switch 38, which is selectively turned on to enable battery 32 to supply power to respective components of unit 10, or turned off to prevent any transmission of power thereto. User interface console 36 further includes a set of buttons or switches 40 for use by an operator in controlling imaging subsystem 24.

To direct the movements of unit 10, a control bar 42 is usefully mounted at the rearward end of console 36. The bar 42 is urged toward column 16 from a center position to move unit 10 forward, and is moved away from column 16 to move the unit rearward. The bar 42 is twisted to the right or left, to steer the unit rightward or leftward, respectively. Control bar 42 and switches 40 collectively comprise a set of operator controls 56 (shown in FIG. 2) which generate various commands or instructions for the operation of unit 10, and more specifically for the respective components and subsystems thereof. These commands are coupled to a system control 44, contained in housing 26 and interactively coupled to battery 32 and subsystems 24 and 30. The system control is described hereinafter in further detail. FIG. 1 further shows user interface 36 provided with a display screen 46, Power On indicator LED 48 and a charge mode indicator LED 50.

Figure 2:
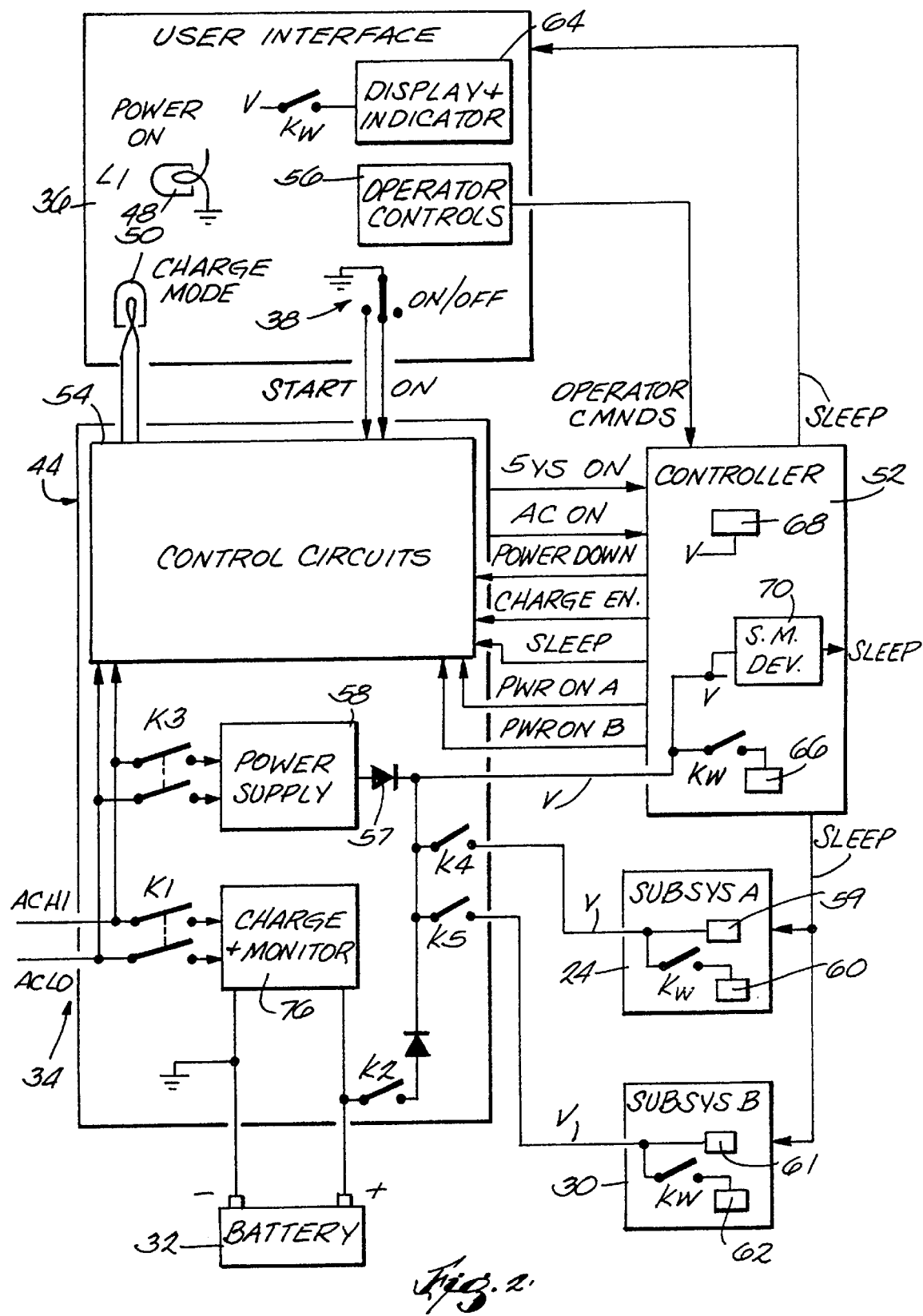
FIG. 2 is a block diagram showing certain components of the imaging unit of FIG. 1 in greater detail.

Referring to FIG. 2, there is shown system control 44 comprising a controller 52 and a set of control circuits 54. The switches 40 and control 42 of user interface console 36 shown in FIG. 1 are collectively represented in FIG. 2 as operator controls 56. FIG. 2 further shows operator commands generated by means of control 56 inputted to controller 52, which generates control signals respectively corresponding thereto, as described hereinafter in greater detail.

Referring further to FIG. 2, there is shown X-ray imaging sub-system 24 and motor drive sub-system 30, respectively connected to receive power from battery 32. More particularly, a circuit or relay K2 is closed when switch 38 of console 36 is operated to turn on unit 10. Unit 10 is thereby placed in a "powered-up mode," whereupon respective components and sub-systems of unit 10 are enabled to draw power from battery 32. Power is supplied to sub-systems 24 and 30 by closing relays K4 and K5, respectively. Relay K4 is closed when an operator command to activate the X-ray imaging sub-system 24 is entered into controller 52, by means of operator controls 56. In response, a "Pwr On A" control signal is generated by the controller and coupled to the control circuits 54, which operate to close relay K4. Similarly, motor drive sub-system 30 is activated by an operator command to controller 52, which causes a "Pwr On B" control signal to be generated. Such control signal is coupled to control circuits 54, causing relay K5 to be closed.

It is to be noted that sub-systems 24 and 30 are respectively referenced in FIG. 2 as Subsystems A and B. This is to emphasize the generic nature of the interconnection of sub-systems 24 and 30 with respect to battery 32 and system control 44. That is, unit 10 could have different or additional sub-systems, which were powered and controlled in the same manner as described herein in regard to sub-systems 24 and 30, and the present invention would apply thereto.

When relays K2 and K4 are closed as described above, X-ray imaging sub-system 24 is placed in a "powered-up mode". Thereupon, sub-system 24 draws a minimal amount of power, in order to perform certain tasks in support of and preparatory to the central function of sub-system 24, i.e., X-ray imaging. Such supporting functions include, though are not necessarily limited to, software loading and the establishment and maintenance of a communications path with the controller 52. Components for respectively performing such functions are collectively represented in FIG. 2 by reference numeral 59, and receive power of voltage V from battery 32. In addition, when sub-system 24 is in a powered-up mode, other components thereof, which are directly related to and essential for the X-ray imaging task of the sub-system, are also disposed to draw power from battery 32. These components are collectively represented in FIG. 2 by the reference numeral 60, and include, though are not necessarily limited to, inverter, rotor controller and filament drive logic, and operational amplifiers. It is to be understood that components 60 can draw power even if a command has not been generated by controls 56 to actually perform an X-ray imaging procedure. Delays in carrying out the imaging procedure are thereby reduced or eliminated.

In like manner, motor drive sub-system 30 is placed in a powered-up mode when relays K2 and K5 are closed. In like manner also, sub-system 30 includes two sets of components, both disposed to receive power of voltage V from battery 32, when sub-system 30 is powered-up. Such components are respectively shown in FIG. 2 as component sets 61 and 62. The components 61 perform functions such as software loading and communication with controller 52. Components 62 include, but are not necessarily limited to, drive system electronics such as operational amplifiers, motors, brakes and interface logic. Components 62 are disposed to draw power from battery 32 in preparation of a command from controls 56 to move unit 10, before such command has been generated.

Referring further to FIG. 2, there are shown displays and indicators of user interface console 36 collectively represented by the reference numeral 64. FIG. 2 also shows certain controller function components 66. When relay K2 is closed, unit 10 is generally placed in a powered-up mode whether or not a sub-system thereof is powered up by closing a relay such as K4 or K5. When unit 10 is powered-up, both display and indicator components 64 and controller components 66 draw power from battery 32. Unit 10 has a powered-up mode, of course, to avoid delay when operator commands are subsequently generated to perform useful work, such as acquiring X-ray exposures or moving the unit from one place to another. However, as stated above, up to 25% of the power usage of battery 32 can represent power drawn simply by powered up components, of the sub-systems, controller or interface, at times when none of the sub-systems have been directed to perform their respective intended work functions. Such needless use of power increases the chance that the battery, a limited capacity device, will run out of power at a time when one or more of the work functions must be performed. Such occurrence could be particularly undesirable, or even serious, in a health care environment.

Accordingly, to reduce battery usage while still allowing "powered-up" mode operation to some extent, controller 52 is provided with a sleep mode device 70. Generally, sleep mode device 70 monitors, or is responsive to, the amount of time which passes during which no commands are generated by operator controls 56, or received by controller 52. When such time exceeds a specified time period $T_1$, device 70 generates a sleep mode (Sleep) signal. The sleep mode signal has the effect of opening a number of relays in unit 10, depicted in FIG. 2 as $K_W$. Opening each of the relays $K_W$ causes power to be respectively disconnected from components 60, 62, 64 and 66. Unit 10 is thereby placed into a sleep mode, wherein only components such as 59 and 61 of the sub-systems and 68 of controller 52 continue to draw power.

Components 68, as well as components 59 and 61 described above, are generally limited to communication and interface logic devices necessary to monitor the generation of subsequent operator commands. Components 68 further include devices needed to support controller receipt of any subsequent operator commands, to avoid the need to reboot the system (e.g., main microprocessor), and to supply minimum power needed for such limited activities. The Power On indicator light 48 also remains on during sleep mode. By continuing to supply power to components 59, 61 and 68 during sleep mode, unit 10 is able to quickly wake up, i.e., to respond to any operator command occurring while the unit is in sleep mode. When such command occurs, the unit returns to the powered-up mode, which requires significantly less time than would be necessary to power up from a condition in which all power had been shut off to respective components of unit 10. This would happen if power switch 38 was turned off.

Usefully, sleep mode device 70 is further designed to monitor a second time period $T_2$, commencing when unit 10 enters the sleep mode. If no command signals are generated or received by controller 52 during such second period, device 70, at the conclusion thereof, will generate a power-down signal. The power-down signal turns off key switch 38, so that no further power is drawn from battery 32 unless the system is completely restarted.

Figure 3:
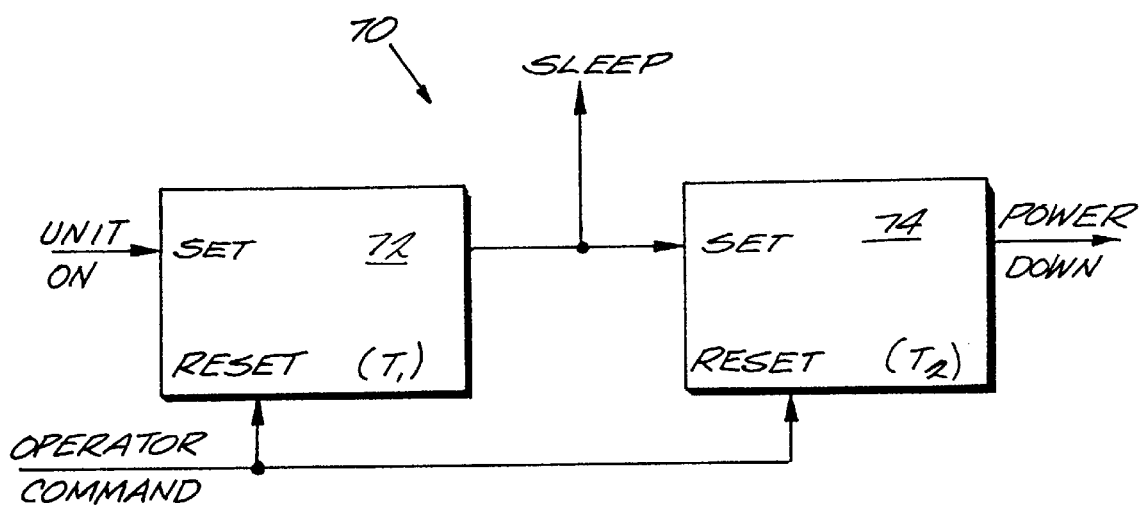
FIG. 3 is a simplified representation of a sleep mode control device for use with the unit of FIG. 1.

If controller 52 comprises a computer related system, sleep mode device 70 can be implemented in software. In an alternative embodiment, device 70 could comprise an arrangement of counters 72 and 74, as shown in FIG. 3. Counter 72 is set or activated by a unit ON signal, generated by turning on key switch 38 to power up unit 10. Counter 72 is configured to count for the time period $T_1$, whereupon it generates an output. However, counter 72 is reset by each operator command. Thus, it will not generate an output unless no command occurs for the time $T_1$. Accordingly, the output of counter 72 can be used for the sleep mode signal.

Referring further to FIG. 3, there is shown counter 74 activated by the sleep mode signal from counter 72 to time the period $T_2$. However, counter 74 is also reset by respective operator commands. Thus, counter 74 will only time the period $T_2$, to produce an output comprising the power-down signal, if no operator commands are received during sleep mode.

Usefully, device 70 is designed so that the time periods $T_1$ and $T_2$ can be selectively adjusted by a user of unit 10. For example, sleep mode period $T_1$ could be a time selected from the range 1 minute to 30 minutes. Similarly, $T_2$ could be a time selected from the range 1 minute to 30 minutes.

A mobile device such as unit 10 may spend twelve or more hours a day plugged into a wall outlet in a battery charging state. If charging continues longer than is necessary, undo stress may be placed on the battery and/or an associated charging circuit. Accordingly, referring again to FIG. 2, there is shown unit 10 provided with a battery charging/charge monitor circuit 76. Circuit 76 generally comprises a circuit arrangement disposed to receive power, through power cord 34, from an AC source(e.g., an "AC HI" source of 220 volts or an "AC LO" source of 110 volts) to supply power of DC voltage to recharge battery 32. Moreover, charging circuit 76 monitors the stored energy level of battery 32. Operation of circuit 76 is directed by controller 52 in accordance with the flow diagram shown in FIG. 4. As an additional measure to conserve power of battery 32, a power supply 58 is provided, which is coupled to an AC source and driven thereby, by operation of relay K3. Relay K2 is opened, and power is provided to the sub-systems from supply 58 through a diode 57. Thus, battery power is not used at all during the charge cycle, to extend battery life.

Figure 4A:
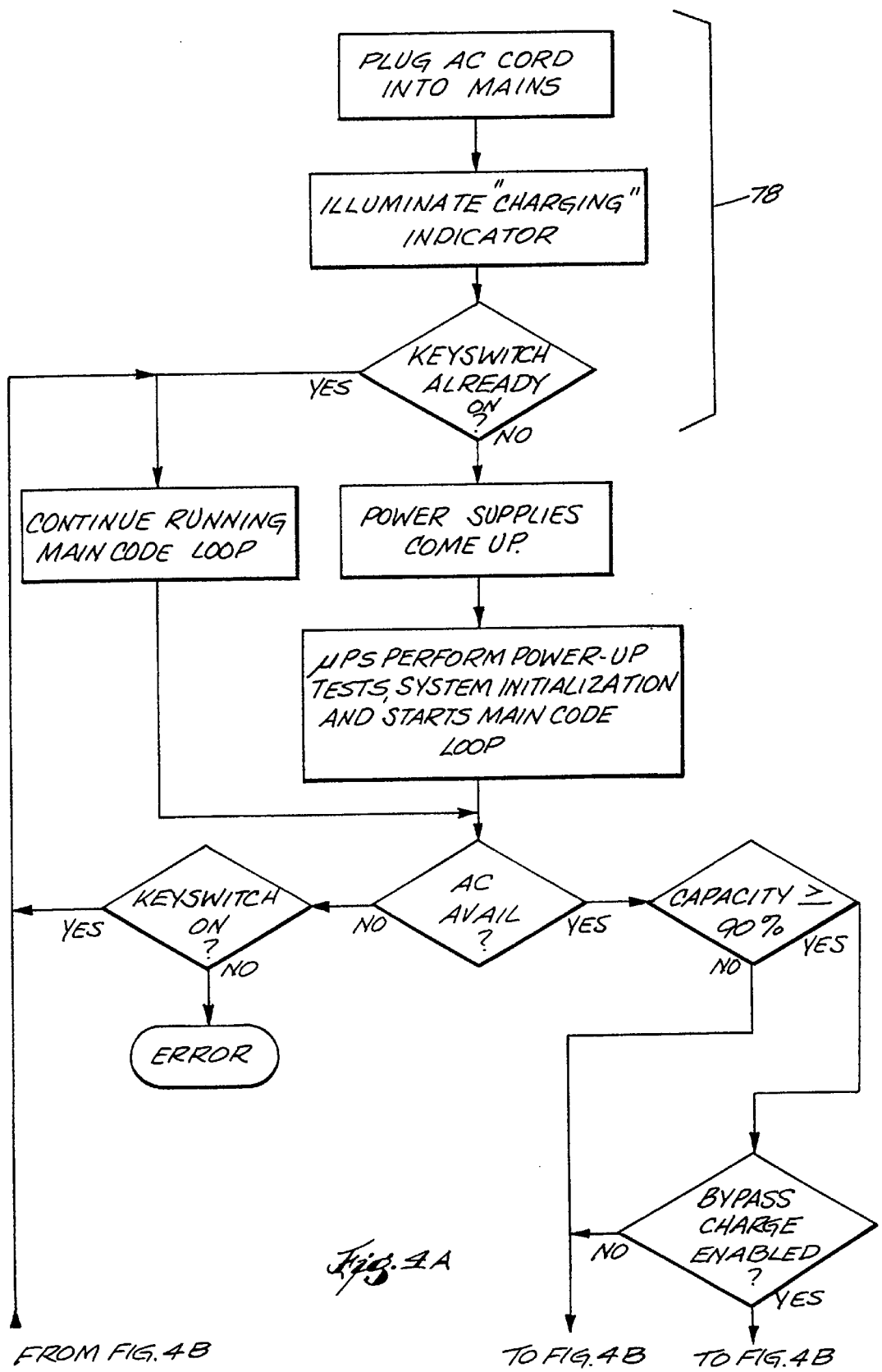

Referring to FIG. 4, there are shown preliminary steps 78 for the battery recharging process, including plugging cord 34 into an AC source and illuminating charge mode indicator LED 50 as a yellow light. Thereupon, a charge enable signal is generated by controller 52, K3 closes and power supply 58 comes up. Microprocessors residing in the controller 52 perform power up, tests, and system initialization, and also start the main code loop, if necessary. When the main code loop is running, the availability of AC power is considered. AC power is made available to battery 32 by closing relay K1. If AC power is available, the level of energy already stored in the battery is observed. If the energy level is 90% or more of the maximum energy capacity of battery 32, the charging operation may be bypassed, thereby avoiding stress associated with recharging and enhancing battery life. Otherwise, the charging cycle is started, and continues until completed. Thereupon, charge mode indicator LED 50 turns green, and the charging circuit is shut down, along with other components of unit 10. Thereafter, the only power drawn is the power required for the green LED.

Obviously, many modifications and variations of the present invention are possible in light of the above teachings. It is therefore understood that within the scope of the disclosed inventive concept, the invention may be practiced otherwise than as specifically described.

What is claimed is:

1. Control apparatus for a medical diagnostic imaging system, wherein said imaging system has a powered-up mode and comprises a power storage device and a number of sub-systems, each of said sub-systems disposed to draw power from said storage device to perform an associated task when a control signal corresponding to the task is generated, a given one of said sub-systems including specified components disposed to receive power from said storage device when said imaging system is in said powered-up mode, even in the absence of a control signal corresponding to the associated task of said given sub-system, and wherein said control apparatus comprises:

entry means for enabling an operator to generate input commands, at least some of said commands respectively causing said corresponding control signals to be generated;

system control means responsive to said input commands for selectively connecting said storage device to and disconnecting said storage device from respective sub-systems;

sleep mode means included in said system control means for disconnecting a sub-set of said specified components from said storage device at the end of a first time period, if said imaging system is in said powered-up mode and no command is received by said system control means during said first time period; and power shut-off means included in said system control for taking said imaging system out of said powered-up mode after disconnection of said component sub-set from said storage device, if no command is received by said system control means prior to the end of a second time period which follows said first time period.

2. The apparatus of claim 1 wherein said system control means comprises:

a system controller for generating control signals which respectively represent said commands; and a set of control circuits operable in response to said control signals to selectively couple power from said storage device to said sub-systems.

3. The apparatus of claim 2 wherein:

said apparatus enables an operator to adjust the respective lengths of said first and second time periods.

4. The apparatus of claim 2 wherein:

said system controller is disposed to generate a first control signal to activate a first sub-system while a second sub-system remains inactive.

5. The apparatus of claim 4 wherein:

said first sub-system comprises a sub-system for acquiring X-ray images, and said second sub-system comprises a sub-system for enabling an operator to selectively move said imaging system.

6. The apparatus of claim 3 wherein:

said apparatus includes charging means for increasing the amount of power contained in said storage device, until said amount reaches a specified maximum.

7. The apparatus of claim 6 wherein:

said charging means comprises means for by-passing a battery charge operation when the energy level of the battery is at a specified percentage of maximum battery energy capacity.

8. Control apparatus for a medical diagnostic imaging system, wherein said imaging system comprises a power storage device and a number of components disposed to perform functions respectively corresponding thereto, said control apparatus comprising:

entry means for generating commands to selectively direct said components to perform their respectively corresponding functions;

system control means for initially coupling each of said components to receive power from said storage device;

sleep mode means included in said system control means for decoupling a first set of said components from said storage device, while allowing a second set of said components to remain coupled to said storage device, following a first time period during which no command is generated by said entry means, wherein each component of said second set performs a function which is required to enable said system control means to recognize that a command has been generated by said entry means; and means included in said system control means for decoupling said second set of components from said storage device if no command is generated by said entry means prior to the end of a second time period following said first time period.

9. The apparatus of claim 8 wherein said system control means comprises:

a system controller for generating control signals which respectively represent said commands; and a set of control circuits operable in response to said control signals to selectively couple power from said storage device to said components of said first and second sets.

10. The apparatus of claim 9 wherein:

said imaging system comprises a mobile imaging system and said storage device comprises a battery; and said imaging system includes a first sub-system for acquiring X-ray images, and a second sub-system for enabling an operator to physically move said imaging system.

11. The apparatus of claim 10 wherein:

said apparatus includes charging means for increasing the amount of power contained in said battery, until said amount reaches a specified level.

* * * * *